US00PP22615P2

(12) United States Plant Patent
Smith

(10) Patent No.: US PP22,615 P2
(45) Date of Patent: Apr. 3, 2012

(54) ***CHRYSANTHEMUM* PLANT NAMED 'SYNJAC PERL'**

(50) Latin Name: *Chrysanthemum×morifolium*
Varietal Denomination: Synjac Perl

(75) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 19 days.

(21) Appl. No.: 12/925,229

(22) Filed: Oct. 15, 2010

(51) Int. Cl.
*A01H 5/00* (2006.01)

(52) U.S. Cl. ..... Plt./288

(58) Field of Classification Search ..... Plt./288
See application file for complete search history.

*Primary Examiner* — June Hwu
(74) *Attorney, Agent, or Firm* — S. Matthew Edwards

(57) ABSTRACT

A new *Chrysanthemum* plant named 'Synjac Perl' particularly distinguished by the small to medium sized flowers with white ray florets, dark yellow-green foliage, nice compact and mounded plant habit and a natural flowering season in later September.

1 Drawing Sheet

Latin name of the genus and species of the plant claimed: *Chrysanthemum×morifolium.*

Varietal denomination: 'Synjac Perl'.

BACKGROUND OF THE NEW PLANT

The present invention comprises a new *Chrysanthemum*, botanically known as *Chrysanthemum×morifolium*, and hereinafter referred to by the variety name 'Synjac Perl'.

'Synjac Perl' is a product of a planned breeding program. The new cultivar has small to medium sized flowers with white ray florets, dark yellow-green foliage, nice compact and mounded plant habit and a natural flowering season in later September.

'Synjac Perl' originates as a natural whole plant mutation of an unpatented, proprietary plant designated '03-M345D'. 'Synjac Perl' was discovered outdoor in a large quantity trial format and selected by the inventor as a single flowering plant within a population of the parent cultivar in a controlled breeding program in Alva, Fla. in November 2007. The parent cultivar has white and pink flowers and a natural flowering season that is a couple days slower.

The first act of asexual reproduction of 'Synjac Perl' was accomplished when vegetative cuttings were propagated from the initial selection in December 2007 in a controlled environment in Alva, Fla.

BRIEF SUMMARY OF INVENTION

Horticultural examination of plants grown from cuttings of the plant initiated in December 2007, and continuing thereafter, has demonstrated that the combination of characteristics as herein disclosed for 'Synjac Perl' are firmly fixed and are retained through successive generations of asexual reproduction.

'Synjac Perl' has not been observed under all possible environmental conditions. The phenotype may vary significantly with variations in environment such as temperature, light intensity and day length.

A Plant Breeder's Right for this cultivar was applied for in Canada on Oct. 30, 2009 (09-6768). 'Synjac Perl' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'Synjac Perl' with colors being as true as possible with an illustration of this type. The photographic drawing shows a flowering potted plant of the new variety, and a close-up of the flowers. These plants were approximately 10 weeks of age.

DETAILED BOTANICAL DESCRIPTION

The plant descriptions and measurements were taken in Gilroy, Calif. in June 2010 under natural light. These plants were about 12-13 weeks old.

The aforementioned photographs were taken in Gilroy, Calif. in mid-May 2010 outdoors. All were grown in a greenhouse trial.

Color references are made to The Royal Horticultural Society Colour Chart (R.H.S.) 2001.

TABLE 1

DIFFERENCES BETWEEN THE NEW VARIETY 'SYNJAC PERL' AND A SIMILAR VARIETY

| | 'Synjac Perl' | 'GEDI-M1' (U.S. Plant Pat. No. 11,235) |
|---|---|---|
| Flower size: | Slightly larger | Slightly smaller |
| Flower type: | More decorative/less pom-pom form | Less decorative/more pom-pom form |
| Plant size: | Larger | Smaller |
| Plant habit: | More ball/less mounded | Less ball/more mounded |

Plant:
*Form, growth and habit.*—Herbaceous decorative garden type; stems upright and outwardly spreading, freely branching, strong and moderately vigorous growth habit.
*Plant height.*—12-13 cm.
*Plant height (inflorescence included).*—15-17 cm.
*Plant width.*—12-14 cm.
*Garden performance and tolerance to weather.*—Very good.

Roots:
*Number of days to initiate roots.*—4 days at about 22 degrees C.
*Number of days to produce a rooted cutting.*—10-12 days at 22 degrees C.
*Type.*—Fine, fibrous, free branching.
*Color.*—RHS N155B but whiter.

Foliage:
*Arrangement.*—Alternate, simple.
*Immature, leaf color, upper surface.*—RHS 147A.
*Lower surface.*—Closest to RHS 138A but a little more yellow-green.
*Mature, leaf color, upper surface.*—RHA 147A.
*Lower surface.*—Closest to RHS 138A but a little more yellow-green.
*Length.*—3.5-4.0 cm.
*Width.*—2.6-2.8 cm.
*Shape.*—Ovate.
*Base shape.*—Attenuate.
*Apex shape.*—Mucronulate.
*Margin.*—Slightly and irregularly lobed; serrate.
*Texture, upper surface.*—Bifid T-shaped hairs.
*Lower surface.*—Bifid T-shaped hairs.
*Color of veins, upper surface.*—RHS 144B basally, but indistinct otherwise.
*Color of veins, lower surface.*—RHS 144B basally, but indistinct otherwise.
*Petiole color.*—RHS 144B.
*Length.*—0.5 cm.
*Diameter.*—0.15-0.2 cm.
*Texture.*—Bifid T-shaped hairs.

Stem:
*Quantity of main branches per plant.*—About 6.
*Color of stem.*—RHS 146B.
*Length of stem.*—9-11 cm.
*Diameter.*—0.2-0.3 cm.
*Length of internodes.*—0.6-1.0 cm.
*Texture.*—Bifid T-shaped hairs.
*Color of peduncle.*—RHS 146B.
*Length of peduncle.*—5-6 cm.
*Peduncle diameter.*—0.1 cm.
*Texture.*—Bifid T-shaped hairs.

Inflorescence:
*Type.*—Compositae type, solitary inflorescences (decorative-type) borne terminally above foliage, ray florets arranged acropetally on a capitulum.
*Natural season flowering.*—About mid-September.
*Quantity of inflorescences per plant.*—About 65.
*Lastingness of individual blooms on the plant.*—About 3-4 weeks.
*Fragrance.*—Very slightly spicy.

Bud (just when opening/showing color):
*Color.*—RHS N155B but whiter.
*Length.*—0.6-0.8 cm.
*Width.*—0.6-0.7 cm
*Shape.*—Oblate. .

Immature inflorescence:
*Diameter.*—3.0 cm.
*Color of ray florets, upper surface.*—RHS N155B but whiter.
*Lower surface.*—RHS N155B but whiter.

Mature inflorescence:
*Diameter.*—3.5-4.0 cm.
*Depth.*—2.0 cm.
*Total diameter of 'disc'.*—0.4 cm; but cannot see this unless you separate the inner petals.
*Receptacle height.*—0.3-0.4 cm.
*Receptacle diameter.*—0.3-0.4 cm.

Ray florets:
*Average quantity of florets.*—About 100 in numerous whorls.
*Color of florets, upper surface.*—Closest to RHS N155B but whiter; (If grown in cooler temperatures, these florets can have a little pinkish coloring to them, about RHS N78C in varying hues/shades, but was not seen on these plants for descriptions here).
*Lower surface.*—Closest to RHS N155B but whiter.
*Length.*—0.7-0.9 cm.
*Width.*—0.35-0.4 cm.
*Shape.*—Oblong.
*Apex shape.*—Slightly praemorse to irregularly emarginate.
*Margin.*—Entire.
*Texture, upper surface.*—Papillose.
*Lower surface.*—Papillose.

Disc florets:
*Average quantity of florets.*—About 3-13.
*Color of florets.*—RHS 144B with a RHS 1C apex.
*Length.*—0.4 cm.
*Width.*—0.1 cm.
*Shape.*—Tubular, elongated.
*Apex shape.*—Acute, 5 pointed.

Phyllaries:
*Quantity.*—About 23-25.
*Color, upper surface.*—RHS 137A.
*Lower surface.*—RHS 137A.
*Length.*—0.4 cm.
*Width.*—0.15 cm.
*Shape.*—Lanceolate.
*Apex shape.*—Acute.
*Based.*—Fused.
*Margins.*—Entire; papery margins.
*Texture, upper surface.*—Glabrous, glossy.
*Lower surface.*—Bifid T-shaped hairs.

Reproductive organs:
*Pistil.*—1.
*Found on both florets.*—Yes.
*Length.*—0.3-0.4 cm.
*Style color.*—RHS N144D and more translucent looking.
*Style length.*—0.2-0.3 cm.
*Stigma color.*—RHS 3C.
*Stigma shape.*—Bi-parted.
*Ovary color.*—Not observed.
*Stamens.*—1.
*Found on disc florets only.*—Yes.
*Color of filaments.*—RHS N144D.
*Length filaments.*—0.3 cm.
*Anther color.*—RHS 8B.
*Anther length.*—0.1 cm.

*Anther shape*.—Ovate.

*Color of pollen*.—Not observed.

*Pollen amount*.—Not observed.

*Fertility/seed set*.—Has not been observed on this hybrid.

Disease/pest resistance: Disease/pest resistance has not been observed on this hybrid.

What is claimed is:

1. A new and distinct variety of *Chrysanthemum* plant named 'Synjac Perl' substantially as illustrated and described herein.

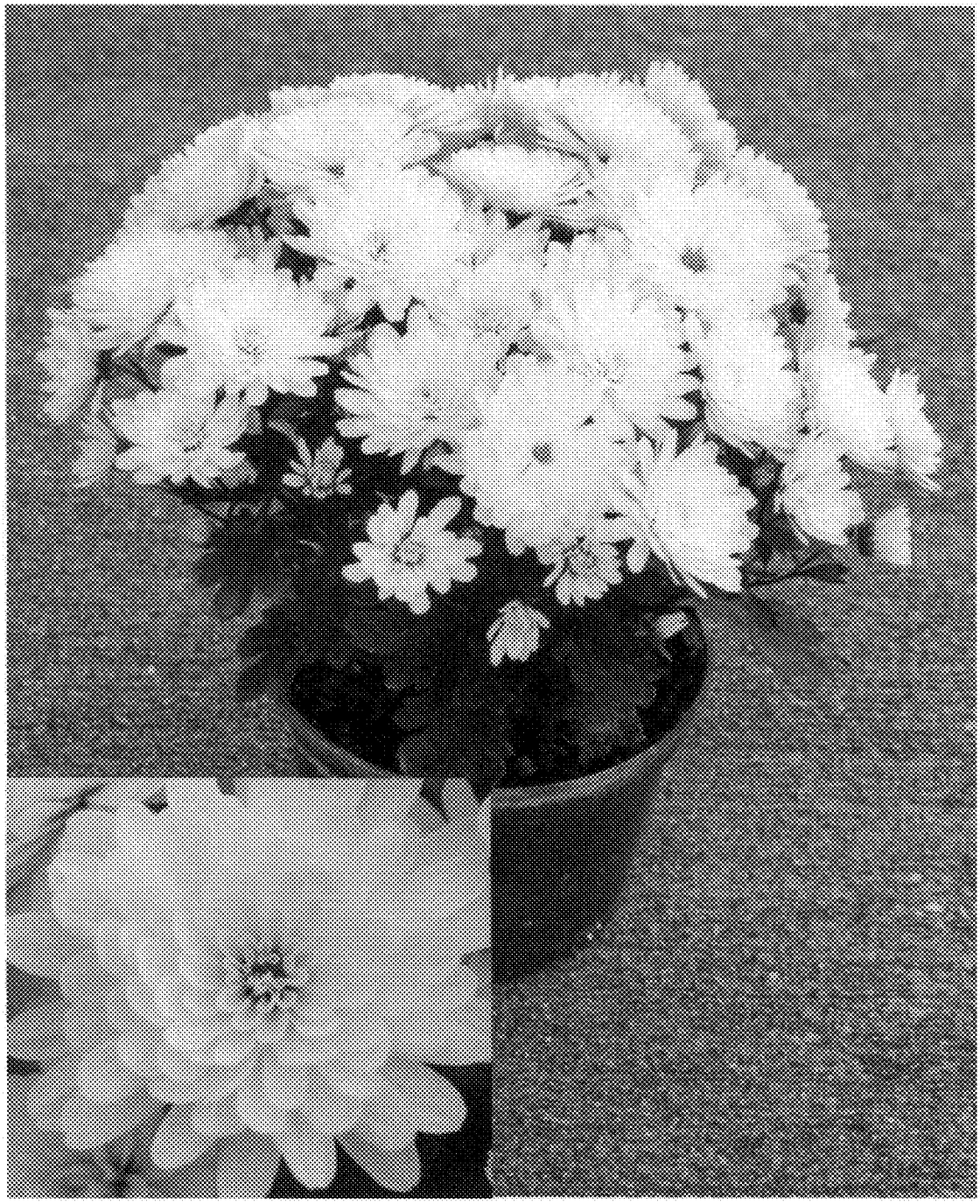

* * * * *